US006323024B1

(12) United States Patent
Tracy et al.

(10) Patent No.: US 6,323,024 B1
(45) **Date of Patent: *Nov. 27, 2001**

(54) COXSACKIE VIRUS VECTORS FOR DELIVERY OF NUCLEIC ACIDS ENCODING ANTIGENIC OR THERAPEUTIC PRODUCTS

(75) Inventors: Steven M. Tracy; Nora M. Chapman, both of Omaha, NE (US); Peter Kolbeck, Carmichael; James M. Malone, III, Redwood, both of CA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/403,672

(22) PCT Filed: Mar. 5, 1998

(86) PCT No.: PCT/US98/04291

§ 371 Date: Mar. 27, 2000

§ 102(e) Date: Mar. 27, 2000

(87) PCT Pub. No.: WO98/39426

PCT Pub. Date: Sep. 11, 1998

Related U.S. Application Data

(63) Continuation-in-part of application No. 08/812,121, filed on Mar. 5, 1997, now Pat. No. 6,071,742.

(51) Int. Cl.$^7$ .......................... C12N 15/86; C12N 15/63; C12N 15/19; C07H 21/04

(52) U.S. Cl. .................. 435/320.1; 435/69.1; 435/235.1; 435/455; 435/456; 435/366; 536/23.5; 536/23.51; 536/23.52; 536/24.1; 424/93.1; 424/93.2; 424/93.6

(58) Field of Search ............................... 435/69.1, 235.1, 435/320.1, 455, 456, 366; 424/93.1, 93.2, 93.6; 536/23.5, 23.51, 23.52, 24.1

(56) References Cited

U.S. PATENT DOCUMENTS 6,071,742 * 6/2000 Tracy et al. ....................... 435/320.1

FOREIGN PATENT DOCUMENTS 0 302 801 B1 8/1988 (EP) .

OTHER PUBLICATIONS

Fox, Nature Biotechnology, vol. 18, pp. 143–144, Feb. 2000.*

Kmiec, American scientist, vol. 87, pp. 240–247, May, 1999.*

Anderson, Nature, vol. 392, pp. 25–30, Apr. 1998.*

Leslie, et al., *Clinical and Experimental Aspects of Viral Moycarditis, Clinical Microbiology Reviews* 3:191–203, Apr. 1989.

Oldstone, Michael, B.A., *Minieview: How Virses Escape from Cytotoxic T Lymphocytes: Molecular Parameters and Players, Virology,* 234, 1979–185 (1997).

*Frontiers in Medicine: Vaccines—Bumps on the Vaccine Road, Science,* vol. 265, Sep. 2, 1994.

Zhang et al., *Coxsackievirus B3–Induced Mycarditis, Amer. Journal of Patholyog,* vol. 150, No. 6, Jun. 1997.

Orkin, et al., *Report and Recommendations of the Panel to Asess the NIH Investment in Research on Gene Therapy,* Dec. 7, 1995.

Verma and Somia, *Gene therapy—Promises, Problems and Prospects,* Nature, vol. 398, Sep. 18, 1997.

Chapman and Tracy, *Can Recombinant DNA Technology Provide Useful Vaccines Against Viruses Which Induce Heart Disease*?, European Heart Journal, 16, (1995).

Zell, et al., Coxsackievirus B3 (CVB3) variants expressing cytokine genes as a tool to influence the local immunity in vivo, Institute of Virology, Medical Center, Friedrich Schiller University, Jena, Germany, 1997.

* cited by examiner

*Primary Examiner*—David Guzo
(74) *Attorney, Agent, or Firm*—Woodcock Washburn LLP

(57) ABSTRACT

The present invention is drawn to the use of attenuated Coxsackievirus cardiotropic virus vectors as efficient gene transfer vectors to deliver immunomodulatory or other biologically active proteins and/or antigenic epitopes in transient infections to aid in preventing, ameliorating, and/or ablating infectious viral heart disease and reducing, or ablating entirely, heart transplant rejection. Additionally, other organs or tissues may be targeted with specific picornaviruses. In particular, an attenuated CVB3 viral vector able to express a cytokine is provided. This cytokine-expressing viral vector is able to deliver the cytokine to a target tissue and reduce disease symptoms.

30 Claims, 6 Drawing Sheets

CVB3 aa 836(ID) PLS CVB3 aa 864 (2A)

...SGVTTTRQSITTMTNT/GAFGQQSGAVTLEDPRVPSSNSITTMTNT/GAFGQQSGAVYVG...

mIL-10 (1-178)

...SGVTTTRQSITTMTNT/GAFGQQSGAVTLEMPGSA...MKSNSITTMTNT/GAFGQQSGAVYVG...

FIG. 2

CVB3 N743 CVB3 N746
...ATGGGAAATTCGAGCTCGGTACCCGGGGATCCTCTAGAGTCGACCTGCAGGCATGCGGGTTTTCAAGGA...
M...G... N...S... S... S... V...P... G... D... P... L... E... S... T... C... R... H... A... G... F... Q / G
CVB3 aa2 (1A)

mIL-10(1-178)
...ATGGGAAATTCGAGCTCGATGCCTGGC...ATGAAAAGCGCATGCGGGTTTTCAAGGT
M...G... N...S... S... S... M... P... G...··· M...K...S... H... A... G... F... Q / G

FIG. 3

5' NTR  CASPID PROTEINS      NON-STRUCTURAL PROTEINS
5'|————————CPV/49 Polylinker genome————————|

Protease P2-a cleavage sites

→ POLYLINKER →
A            B

...ACTACTAGGCAAAGCATCACTACAATGACAAATACGGGCGCATTTGGACAACAATCAGGGCAGTCTCGGATCCA... |POLYLINKER...
...T  T  R  Q  S  I  T  T  M  T  N  T  G  A  F  G  Q  Q  S  G  A  V  S  D  P...

...POLYLINKER| *  *   *    *    *  *  *
...GAATTCTGCAGATCAATTACCACCATGACCAACACCGGGGCCGCCATTTGACACAATCAGGGCAG...
...  E  F  C  R  C  I  T  T  M  T  N  T  G  A  F  G  Q  S  G  A  V...
                                            ^ P2-A CLEAVAGE SITE

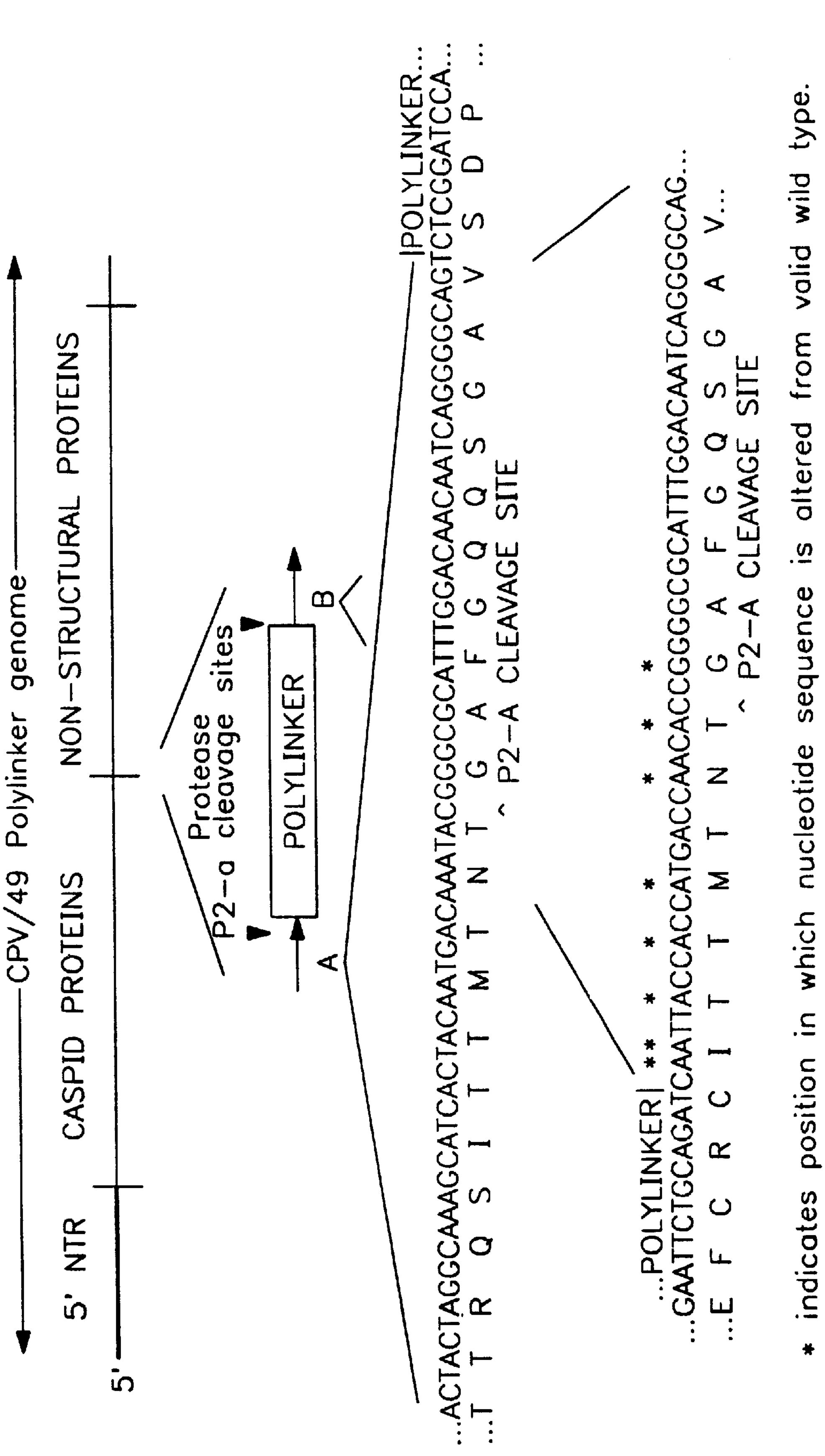

FIG. 4

* indicates position in which nucleotide sequence is altered from valid wild type.

COXSACKIE VIRUS VECTORS FOR DELIVERY OF NUCLEIC ACIDS ENCODING ANTIGENIC OR THERAPEUTIC PRODUCTS

This application claims priority under 35 U.S.C. §120 to and is a continuation-in-part of U.S. patent application No. 08/812,121, filed Mar. 5, 1997, now U.S. Pat. No. 6,071,742, issued Jun. 6, 2000, the entirety of which is incorporated by reference herein.

This invention was produced in part using funds obtained through a grant from the National Institutes of Health. Consequently, the United States government has certain rights in this invention.

FIELD OF THE INVENTION

The present invention relates generally to the fields of molecular biology and virology. More specifically, the present invention relates to a biologically engineered, attenuated Coxsackievirus and its use as a delivery vehicle for nucleic acids encoding antigenic or biologically active proteins.

BACKGROUND OF THE INVENTION

The coxsackieviruses, members of the family Picornaviridae, are divided into two groups, based essentially on their pathogenicity and replication in newborn mice. The Group B coxsackieviruses (CVB) are composed of six serotypes (1–6). Similar to other members of the Picornaviridae, the CVB genome is a single-stranded, messenger sense, polyadenylated RNA molecule (for review see Romero, J. R. et al., *Current Topics in Microbiology and Immunology* 223: 97–152, 1997). Genome analysis of the CVB shows that they are organized into a 5' nontranslating region, a protein coding region containing a single open reading frame, a 3' nontranslated region and a terminal poly-A tail, similar to other Picornaviruses. The CVB protein coding region can be further divided into three regions, P1, P2 and P3. P1 encodes the four capsid proteins VP4 (1A), VP2 (1B), VP3 (1C) and VP 1 (1D); P2 and P3 encode the non-structural proteins required for the CVB lifecycle: 2A (protease), 2B, 2C, 3A 3B (Vpg), 3C (protease) and 3D (polymerase) (See Romero et al., 1997, supra).

The genomes of CVB that have been fully sequenced are very similar to one another in length, ranging from 7389 nucleotides (CVB1) to 7402 nucleotides (CVB5) (Romero et al., 1997 supra). Variations in length are due to differences within the coding region of VP1 and VP2 (capsid proteins) and in the 5' and 3' non-translated regions. The 5' non-translated regions also show remarkable similarity in length. For a detailed review of the similarities among the CVB genomes, refer to Romero et al, supra, 1997.

One of the six serotypes of the group B coxsackieviruses, Coxsackievirus B3 (CVB3), has been particularly well studied, and serves as a prototype for the other coxsackieviruses. The CVB3 genome is single molecule of positive sense RNA which encodes a 2,185 amino acid polyprotein. The single long open reading frame is flanked by a 5' non-translated region (5' NTR), 742 nucleotides long, and a much shorter 3' NTR which terminates in a polyadenylate tract. Like the polioviruses (PVs), CVB3 shuts off host cell protein translation in infected HeLa cells. The near atomic structure of the CVB3 virion has been solved, demonstrating that the CVB3 capsid shares a similar capsid structure with genetically-related entero-and rhinoviruses.

Coxsackie B viruses are established etiologic agents of acute human inflammatory heart disease (reviewed in Cherry, J. D. *Infectious Diseases of the Fetus and Newborn Infant*, 4$^{th}$ ed., pp.404–446, 1995) and cardiac CVB3 infections may lead to dilated cardiomyopathy. Systemic CVB3 infections are common in neonates: often severe or life-threatening, they usually involve inflammation and necrosis of the heart muscle. One study of neonates under three months of age suggested a CVB infection rate as high as 360/100,000 infants with an associated 8% mortality (Kaplan, M. H., et al., *Rev. Infect. Dis.* 5:1019–1032, 1983). Acute and chronic inflammatory heart disease afflicts approximately 5–8 individuals per one hundred thousand population annually worldwide (Manolio, T. A., et al. *Am. J. Cardiol.* 69: 1458–1466, 1992). Based upon molecular evidence of enteroviral involvement, approximately 20–30% of cases of acute inflammatory heart muscle disease and dilated cardiomyopathy involve an enteroviral etiology (see, e.g., Kandolf, R. *Coxsackieviruses-A General Update*, p. 292–318, 1988; and Martino, T. A., et al., *Circ. Res.* 74:182–188, 1994).

The inflammatory process which characterizes enterovirus-induced inflammatory heart disease has been extensively studied in murine models (reviewed in Gauntt, C., et al., *Medical Virology*, 8th ed., p. 161–182, 1989; Leslie, K., et al., *Clin. Microbiol. Rev.* 2:191–203, 1989; Sole, M., and P. Liu., *J. Amer. Coll. Cardiol.* 22 (Suppl.A):99A–105A, 1994; and Woodruff, J. F., *Am. J. Pathol.* 101:425–484, 1980), but it remains unclear precisely what specific roles are played by the various components of the cell-mediated immune response in the induction of acute disease and continuation of the chronic state. However, it is clear that in the presence of an intact murine immune system, CVB3-induced inflammatory heart disease develops only following inoculation of mice with a cardiovirulent CVB3 strain (Chapman, N. M., et al., *Arch. Virol.* 135:115–130, 1994; Gauntt, C. J., et al., *J. Med. Virol.* 3:207–220, 1979; Tracy, S., et al., *Arch. Virol.* 122:399–409, 1992; and Woodruff, J. F., and E. D. Kilbourne, *J. Infect. Dis.* 121:137–163, 1970).

Both cardiovirulent (able to induce disease) and non-cardiovirulent strains of CVB3 replicate well in hearts of experimentally-infected mice. Only cardiovirulent CVB3 strains, however, cause the significant cardiomyocyte destruction with subsequent cardiac inflammation which is characteristic of acute myocarditis (Chapman, N. M., et al., *Arch. Virol.* 135: 115–130 (1994); and Tracy, S., et al., *Arch. Virol.* 122:399–409, 1992). Non-cardiovirulent CVB3 is cleared from the experimentally-infected murine heart within 7–10 days post-infection, while infectious cardiovirulent CVB3 can remain detectable in hearts for up to 2 weeks post-infection (Klingel, K., et al, *Proc. Natl. Acad. Sci. U.S.A.* 89:314–318, 1992; Lodge, P. A., et al., *Am. J. Pathol.* 128:455–463, 1987; and Tracy, S., et al., *Arch. Virol.* 122:399–409, 1992). The fall in murine cardiac infectious CVB3 titer is coincident with the rise in anti-CVB3 neutralizing antibody titers and the ability of T cells to recognize CVB3 antigens (Beck, M. A., and S. Tracy, *J. Virol.* 63:4148–4156, 1989; Gauntt, C., et al., *Medical Virology*, 8th ed., p. 161–182, 1989; and Leslie, K., et al., *Clin. Microbiol. Rev.* 2:191–203, 1989). In addition to direct in situ hybridization evidence for enteroviral replication in human heart myocytes and for cardiovirulent CVB3 replication in murine heart myocytes, CVB3 infects a variety of cultured cardiac cell types including murine and human cardiomyocytes, murine fetal heart fibroblasts and cardiac endothelial cells.

Of great interest is that heart transplantation and acute enteroviral heart disease evoke a similar immune response in a host. Acute rejection of a transplanted heart involves primarily a Th1 type T cell response, the same type of T cell response that is observed in CVB3 induction of acute myocarditis in well-studied murine models of CVB3-induced inflammatory heart disease. Switching of this response to the Th2 type response, with a concomitant ablation of disease, has been accomplished in mice through parenteral administration of the key modulatory cytokines IL-4 or IL-10. However, parenteral administration of cytokines to humans often results in undesired clinical side effects.

Thus, the prior art is deficient in the use of an attenuated coxsackievirus as a gene delivery vector, specifically to target immunomodulatory or other biologically active genes or antigenic epitopes to selected cells, tissues or organs, including the heart. Such a mode of administration or gene delivery circumvents the undesirable side effects of parenteral administration of immunomodulatory agents, antigens or other therapeutic molecules. Thus, the present invention fulfills this long-standing need and desire in the art.

SUMMARY OF THE INVENTION

One object of the present invention is to provide viral vectors for therapeutic or prophylactic use in human disease by delivering nucleic acids encoding antigenic epitopes or specific biologically active gene products, such as (but not limited to) immunomodulatory cytokines, to target cells, tissues or organs in an individual.

Thus, according to one aspect of the invention, a viral vector for delivering a heterologous nucleic acid to a target cell, tissue or organ is provided, which comprises a coxsackievirus genome modified to encode an attenuated coxsackievirus, the genome further comprising at least one cloning site for insertion of at least one expressible heterologous nucleic acid. In a preferred embodiment, the coxsackievirus genome is a coxsackievirus B genome, most preferably a coxsackievirus B3 genome.

In one embodiment of the invention, attenuation of the coxsackievirus is achieved by altering a transcription regulatory region of the genome. Preferably, the transcription regulatory region comprises a 5' untranslated region of the genome. In one embodiment, the 5' untranslated region is replaced with a 5' untranslated region of a non-enterovirus genome selected from the group consisting of poliovirus and echovirus. In another embodiment, a coxsackievirus B3 genome is modified by substituting a C or G for a U at nucleotide position 234 of the genome.

The cloning site of the coxsackievirus vector can be positioned between a coding sequence for a capsid protein and a coding sequence for viral protease. In another embodiment, the cloning site is positioned at the start of the genome's open reading frame, and is constructed such that the inserted expressible heterologous DNA comprises a translation start codon and a 3' sequence recognized by a viral protease.

In one embodiment, the expressible heterologous DNA carried by the coxsackievirus vector of the invention encodes an antigenic product. In another embodiment, it encodes a biologically active product, such as a biologically active protein. Preferably, the protein is a cytokine, such as IL-4 or IL-10. Alternatively, the protein could be another immunomodulatory protein, such as B-7 (B-7-1 or B-7-2).

According to another aspect of the present invention, there is provided a bioengineered virus for the therapeutic delivery of at least one heterologous gene to a target organ or organ system in an individual, comprising a Coxsackievirus B3 (CVB3), wherein said Coxsackievirus B3 is attenuated, and wherein a genome of said CVB3 codes for said at least one heterologous gene. Attenuation of the CVB3 may be accomplished through a transcriptional mechanism. Preferred embodiments include attenuating the virus by substituting a cytosine or guanosine nucleotide for a uracil nucleotide at position nt234 in the genome of the coxsackievirus B3. Another preferred embodiment includes point mutations at positions nt233 and nt236 in the genome of the Coxsackievirus B3, or deletion entirely of nt 233–236.

In addition, the 5' non-translated region of the genome of the Coxsackievirus B3 may be substituted with a 5' non-translated region of a genome from a non-enterovirus to achieve attenuation. In a preferred embodiment, the non-enterovirus is a poliovirus or echovirus.

In most preferred embodiments, the genome of the bioengineered Coxsackievirus B3 includes the basic CVB3/0 genome (as reported by Chapman, N. M., et al, *Arch. Virol.* 135: 115–130 (1994)), wherein a coding sequence for a heterologous gene is inserted between a capsid protein coding sequence and a viral protease coding region site. Alternatively, a heterologous gene may be inserted at the start of the open reading frame, directly upstream of capsid protein 1A, start with the initiation codon AUG, and end with a sequence recognized by a viral protease. In this preferred embodiment, an immunomodulatory gene or a gene for an antigenic epitope is used. In a more preferred embodiment, cytokine genes are delivered. In a most preferred embodiment, the cytokine is IL-4 or IL-10. Up to seven cytokine genes may be delivered in one vector. Further, both antigenic epitopes and cytokines may be delivered at the same time. Also, a preferred embodiment utilizes sequences for viral proteases P2-A and P3-C.

A further object of the present invention is to provide a method for suppressing an immune response in an individual, comprising the step of administering the bioengineered therapeutic virus containing an immunomodulatory gene to an individual.

An additional object of the present invention is to provide a method for vaccinating an individual, comprising the step of administering the bioengineered therapeutic virus containing a gene for an antigenic epitope to an individual.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. The appended drawings illustrate preferred embodiments of the invention and should not be considered to limit the scope of the invention.

FIG. 2 shows the amino acid sequence of the PLS-CVB3 genome (SEQ ID NO:11) and the mIL-10-CVB3 genome (SEQ ID NO:12) at the site of the protease 2A cleavage. In this construct, the cloning procedure has been modified to include a polylinker site (PLS) to facilitate the use of the CVB3 as a generic cloning and expression vehicle. Further modifications include non-direct repeat genetic sequences to code for the protease P2-A cleavage site in the nascent polyprotein. The amino acids donated by the PLS are underlined, while the amino acids which form the 2A cleavage recognition signal are double underlined. The sequence of the mIL-10 insertion is shown in bold.

FIG. 3 shows the nucleotide and amino acid sequence of the PLS-CVB3 genome (SEQ ID NO: 13 and 15) and mIL-10-CVB3 (SEQ ID NO: 14, in which nucleotides 1–27 are SEQ ID NO:5 and nucleotides 28–55 are SEQ ID NO:6, and SEQ ID NO: 16) genome at the beginning of the open reading frame. In this construct, the foreign or heterologous sequence is cloned in the open reading frame upstream of the first encoded viral protein. The translational initiation thus occurs at the beginning of the mIL10 sequence (or other sequence of interest). This construct employs either the viral protease 3C to cleave the foreign protein, here modeled as mIL10, from the first viral capsid protein P1-A. The nucleotide and amino acid sequence of the PLS are underlined and the protease 3C recognition site is double underlined. The sequence of the mIL-10 insertion is shown in bold.

FIG. 4 shows the structure of the CPV/49-Polylinker genome. Nucleic acid sequence is SEQ ID NO: 17 (nucleotides 1–60 and 62–75 comprise SEQ ID NO:7 and nucleotides 76–138 are SEQ ID NO:8; amino acid sequence is SEQ ID NO: 18.

DETAILED DESCRIPTION OF THE INVENTION

Figure 1:
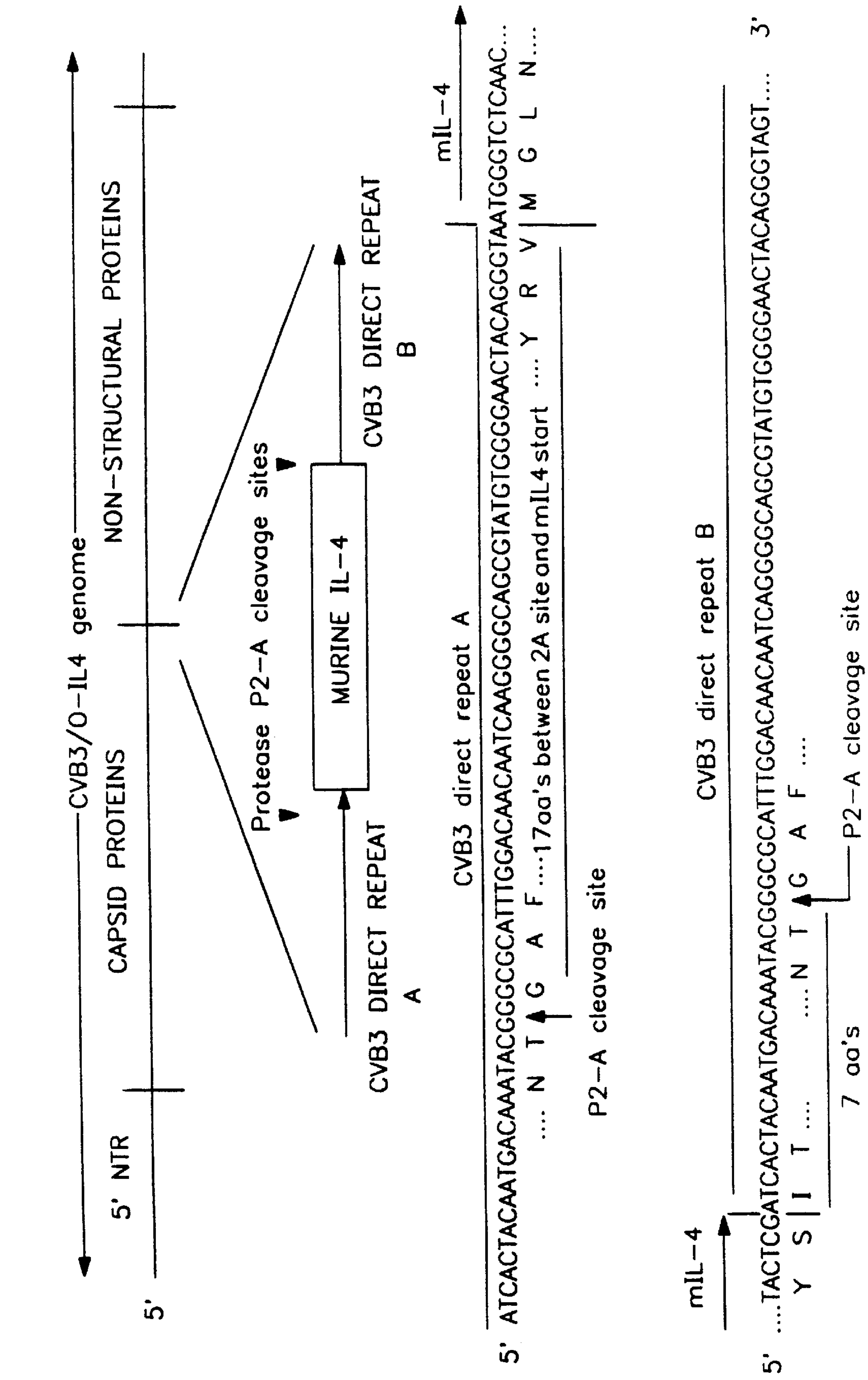
FIG. 1 shows the mIL4 insert in the CVB3/0-IL4 genome. The mIL4 sequence has been cloned between the viral capsid protein P1-D and the viral protease 2A (P2-A). During translation of the viral polyprotein, the most likely mechanism is that the protease P2-A cleaves itself out of the nascent protein in cis and cleaves the site between the capsid protein PI-D and mIL4 sequence in trans. Nucleic acid sequence on top line is SEQ ID NO: 1; nucleic acid sequence on bottom line is SEQ ID NO:2; P2-A cleavage site is SEQ ID NO:9; mIL4 insert is SEQ ID NO:10.

It will be apparent to one skilled in the art that various substitutions and modifications may be made to the invention disclosed herein without departing from the scope and spirit of the invention.

As used herein, the term "Coxsackie B3 virus;" or "CVB3" refers to a specific serotype of the human coxsackie B enterovirus of the family Picornaviridae, genus Eterovirus. The CVB3 genome is characterized by a single molecule of positive sense RNA which encodes a 2,185 amino acid polyprotein.

As used herein, the term "cardiotropic" refers to the targeting of heart tissue by a virus, in this case Coxsackievirus B3.

As used herein, the term "attenuated" refers to a virus, in this case Coxsackievirus B3, that is engineered to be less virulent (disease-causing) than wildtype Coxsackievirus B3.

As used herein, the term "one way viral vector" refers to viral delivery vehicles which are replication deficient for virus production but the RNA genomes of which can autonomously replicate in infected cells for variable periods of time. Such a vector permits replacement of essentially all of the capsid coding region with other sequences of interest, potentially delivering as many as seven cytokine-size coding sequences in the viral genomes. Such genomes made defective through deletion of a polymerase sequence and under a mammalian promoter may be used as a vector for a DNA vaccine or therapeutic, to be delivered by standard means, such as injection or oral administration.

As used herein, the term "basic CVB3/0 genome" shall mean the bioengineered Coxsackievirus B3 as reported by Chapman, N. M., et al, *Arch. Virol.* 122:399–409 (1994).

As used herein, the term "viral protease" or "viral encoded protease" refers to viral encoded enzymes that degrade proteins by hydrolyzing peptide bonds between amino residues. Some such proteases recognize and cleave at only specific sequences.

As used herein, the term "immunomodulatory gene" refers to a gene, the expression of which modulates the course of an immune reaction to a specific stimulus or a variety of stimuli. Examples include interleukin 4, interleukin 10, tumor necrosis factor α, etc.

As used herein, the term "cytokine" refers to a small protein produced by cells of the immune system that can affect and direct the course of an immune response to specific stimuli.

As used herein, the term "antigenic epitope" refers to a sequence of a protein that is recognized as antigenic by cells of the immune system and against which is then directed an immune response, such as an antibody response, for example.

As used herein, the term "viral vector" refers to a virus that is able to transmit foreign or heterologous genetic information to a host. This foreign genetic information may be translated into a protein product, but this is not a necessary requirement for the foreign information.

As used herein, the term "open reading frame" refers to a length of RNA sequence, between an AUG translation start signal and any one or more of the known termination codons, which can be translated potentially into a polypeptide sequence.

As used herein, the term "capsid coding region" refers to that region of a viral genome that contains the DNA or RNA code for protein subunits that are packaged into the protein coat of the virus particle.

In accordance with the present invention there may be employed conventional molecular biology, microbiology, and recombinant DNA techniques within the skill of the art. Such techniques are explained fully in the literature. See, e.g., Sambrook et al., "Molecular Cloning: A Laboratory manual (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); or "Current Protocols in Molecular Biology", eds. Frederick M. Ausubel et al., John Wiley & Sons, 1997.

Therefore, if appearing herein, the following terms shall have the definitions set out below.

A "vector" is a replicon, such as plasmid, phage, cosmid, or virus to which another DNA or RNA segment may be attached so as to bring about the replication of the attached segment. A vector is said to be "pharmacologically acceptable" if its administration can be tolerated by a recipient mammal. Such an agent is said to be administered in a "therapeutically effective amount" if the amount administered is physiologically significant. An agent is physiologically significant if its presence results in a change in the physiology of a recipient mammal. For example, in the treatment of retroviral infection, a compound which decreases the extent of infection or of physiologic damage due to infection, would be considered therapeutically effective.

An "origin of replication" refers to those DNA sequences that participate in the in the initiation of DNA synthesis.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The present invention provides a viral vector for delivering a heterologous nucleic acid to a target cell, tissue or organ, which comprises a coxsackievirus genome modified to encode an attenuated coxsackievirus. The genome further comprises at least one cloning site for insertion of at least one expressible heterologous nucleic acid. Although in a preferred embodiment, the coxsackievirus genome is a coxsackievirus B genome, most preferably a coxsackievirus B3 genome, any coxsackievirus genome is believed to be suitable for use in the present invention. This is due to the high level of organizational similarity among the coxsackieviruses, and indeed among enteroviruses in general (see, e.g., Romero et al., *Current Topics in Microbiology and Immunology* 223: 97–152, 1997, reviewing the genetic relationship among the Group B coxsackieviruses; Chapman et al., *Current Topics in Microbiology and Immunology* 223: 227–258, 1997, reviewing the genetics of coxsackievirus virulence; and Tracy et al., *Trends in Microbiology* 4: 175–179, 1996, reviewing the genetics of coxsackievirus B cardiovirulence and inflammatory heart muscle disease). Thus, in the present invention it has been demonstrated that CVB3 can be attenuated by manipulation of the genome in a variety of ways, most of them relating to altering a transcription regulatory region of the genome, such as the 5' untranslated region of the genome. These alterations are described in greater detail below, and in the examples. Similar manipulations likewise can be made to attenuate any of the other five coxsackievirus B serotypes, as well as coxsackievirus A or other enteroviruses.

It has also been demonstrated in accordance with the present invention that a heterologous DNA segment can be inserted in the CVB3 genome in one of several locations, e.g., between a coding sequence for a capsid protein and a coding sequence for viral protease, or at the start of the genome's open reading frame, in such a manner that the heterologous DNA comprises a translation start codon and a 3' sequence recognized by a viral protease. These insertions are described in greater detail below, and in the Examples. Similar insertions likewise can be made in the genomes of the other coxsackieviruses or other enteroviruses, and successful expression of these heterologous nucleic acids also is expected. Moreover, one skilled in the art also will appreciate that other useful insertion sites exist and can be exploited in the coxsackievirus genome.

Concerning the size of the heterologous nucleic acid that can be inserted into a coxsackievirus vector of the invention, it has been discovered that the genome can incorporate an insert encoding up to 200–400 amino acids. The size of the insert may be increased (e.g., to inserts encoding 800–1,000 amino acids), if certain portions of the genome (e.g., capsid protein coding sequences) are deleted. In this embodiment, it would be necessary to supply a helper virus to provide the missing capsid proteins in trans, for packaging the virus. Such manipulations of viral vectors are well known to persons skilled in the art.

The heterologous nucleic acid sequence carried by the coxsackievirus vector of the invention can encode any gene product, including RNA of any kind, peptides and proteins. In one embodiment, the expressible heterologous DNA carried by the coxsackievirus vector of the invention encodes an antigenic product. In another embodiment, it encodes a biologically active product, such as a biologically active protein. Preferably, the protein is a cytokine, such as IL-4 or IL-10, as described in greater detail below and in the examples.

Particularly preferred aspects of the present invention are directed to a bioengineered virus for the therapeutic delivery of at least one heterologous gene to a target organ or organ system in an individual, comprising a Coxsackievirus B3, wherein said Coxsackievirus B3 is cardiotropic and attenuated, and wherein the genome of the CVB3 codes for the at least one heterologous gene.

It is contemplated additionally that the present invention provides (1) a method for suppressing an immune response in an individual, comprising administering the coxsackievirus vector containing an immunomodulatory gene to an individual and (2) a method for vaccinating an individual, comprising administering a coxsackievirus containing a gene for an antigenic epitope to an individual.

For gene delivery applications, a person having ordinary skill in the art of molecular biology, gene therapy and pharmacology would be able to determine, without undue experimentation, the appropriate dosages and routes of administration of the novel coxsackievirus gene delivery vector of the present invention.

One specific object of the present invention is to use artificially attenuated cardiotropic virus vectors as efficient gene transfer vectors to deliver immunomodulatory proteins and/or antigenic epitopes in transient infections to aid in preventing, ameliorating, and/or ablating infectious viral heart disease. The invention encompasses reducing, or ablating entirely, heart transplant rejection through therapeutic use of immunosuppressive cytokines delivered by attenuated cardiotropic virus vectors. The invention is equally applicable to other inflammatory diseases or conditions of a variety of organs. In this aspect, the invention thus requires three elements: First, an attenuated CVB3 viral vector must be provided. Second, the CVB3 viral vector must be able to express an immunomodulatory protein, such as a cytokine. Third, the vector must be able to deliver the immunomodulatory protein to the target tissue and observably reduce disease symptoms. These three elements are provided in the present invention. Cardiovirulence of CVB3 has been reduced to complete attenuation for heart disease by the substitution of the entire 5' NTR with that of a non-coxsackie enterovirus. The murine cytokine IL-4 (mIL-4) has been expressed within the open reading frame of an attenuated CVB3 strain and has been demonstrated to be biologically active. Inoculation of the CVB3 chimera expressing mIL-4 into mice 1 or 3 days post-inoculation with a pancreovirulent CVB4 strain significantly ablates CVB4-induced pancreatic disease. These data exemplify the unique therapeutic approach to inflammatory diseases of the present invention, and are described in detail in the examples that follow.

The following examples are given for the purpose of illustrating various embodiments of the invention and are not meant to limit it in any fashion.

EXAMPLE 1

Artificial Attenuation of CVB3 for Cardiac Disease in Mice

It has been demonstrated that 5' NTRs of related enteroviruses could be exchanged and viable progeny virus produced when a poliovirus type 1 5' NTR was replaced with some or all of a CVB3 5' NTR (Johnson V. H., and B. L. Semler, *Virology* 162(1):47–57 (1988); and Semler B. L., et al., *Proc-Natl Acad Sci USA* 83(6): 1777–81 (1986)). For the present invention, a variety of CVB3 strains with genomes chimeric in the 5' and/or 3' non-translated regions (NTR) sequences has been constructed from poliovirus type 1. The construct that consists of the 5' NTR from PV1/Mahoney and the remainder of the genome from CVB3/20 has been used most extensively in the investigation of the current invention.

Five passages of this chimeric virus, CPV/49 (FIG. 4), did not result in genetic alteration in the donated poliovirus 5' NTR on the basis of sequence analysis. Replacement of a cardiovirulent CVB3 5' NTR with the homolog from the neurovirulent PV1 Mahoney strain results in a progeny virus that is (a) genetically stable in cell culture in terms of maintaining the PV sequence of the 5' NTR; and (b) highly attenuated for its ability to induce myocarditis in mice, and replicates to 3–4 logs lower titer in the murine heart relative to the parental cardiovirulent CVB3/20 strain. Notwithstanding this attenuation, antibody titers are induced against CVB3 in the inoculated mice that prevent cardiac disease when the mice are challenged with inoculation by a cardiovirulent CVB3 strain.

These data demonstrate that a CVB3 virus strain made chimeric with the replacement of the 5' NTR from PV1 results in a CVB3 strain that is stably attenuated for heart disease when measured in mice and animals, and, furthermore, acts as a vaccine strain by preventing heart disease due to challenge by cardiovirulent CVB3 infection. Thus, such a virus strain acts as a delivery system as envisioned in the present invention.

In addition, the mechanism by which a non-cardiovirulent CVB3 strain (CVB3/0) is attenuated for cardiovirulence has been mapped and identified. By comparison of the complete nucleotide sequences of the avirulent and cardiovirulent CVB3 strains and analyzing a series of intratypic chimeric viruses designed to test the potential genetic sites, a single site nt234 was demonstrated to be the sole site that affected cardiovirulence in these virus strains (Tu Z., et al., *J Virol* 69:4607–18(1995)). The nt234 is U in the cardiovirulent strain, and C in the avirulent strain. Assay in murine heart cells demonstrated little or no detectable differences in Western blotted viral proteins between the two strains, but at least a ten-fold disparity in viral RNA transcription rate was identified. Further work has shown that the normally high positive to negative viral RNA strand ratio in infected cells is significantly altered to near unity when nt234 is C rather than U.

Two further observations make it clear that alteration of certain 5' NTR sequences results in attenuation. One is that mutation of nt234U to G also results in attenuation by what appears to be a similar mechanism to that observed for nt234 C. Second, mutation of this same nucleotide to G in PV1/Mahoney also results in a strain of virus that grows less robustly in HeLa cells than the parental virus. Because nt234 is conserved as U in all enteroviral RNAs examined so far (Chapman N. M., et al., *J. Med. Virol.* 52: 258–261, 1997), as are the surrounding 5 nucleotides 5'-CGUUA (nt234 is underlined), mutation at this site appears to be generally deleterious for enterovirus health. A CVB3 strain, chimeric in the 5' NTR using the PV1 sequence with the added mutation of G instead of U at the PV equivalent of nt234 provides a stably attenuated (but possibly quite weak) CVB3 strain, even less prone to reversion to cardiovirulence than the stably attenuated CVB3/PV1 chimeric described above. Either of these chimeric CVB3 strains is suitable for the viral delivery vector of the present invention in which murine interleukins are expressed within the open reading frame of an artificially attenuated CVB3 strain.

EXAMPLE 2

Successful Expression of Biologically Active Murine IL-4 from Within the CVB3 Open Reading Frame One viral vector construct envisioned by the present invention is depicted in FIG. 1. Acute rejection of a transplanted heart involves primarily a Th1 type T cell response, the same type of T cell response that is observed in CVB3 induction of acute myocarditis in well-studied murine models of CVB 3-induced inflammatory heart disease. Switching of the response to the Th2 type response causes a concomitant ablation of disease. Due to the interest in increasing Th2 type responses, expression of the murine IL-4 gene (mIL-4) was chosen. The virus vector used was the infectious cDNA clone of CVB3/0, a CVB3 strain effectively attenuated for murine heart disease through the mutation at nt234 (from U to C). The mIL-4 sequence contained the signal sequence to facilitate extracellular transport of the expressed interleukin protein (see Sideras P., et al., *Adv Exp Med Biol* 213:227–23.6 (1987)). Flanking the mIL-4 insert were cloned identical sequences that are recognized by the CVB3 protease 2A. The mIL-4 insert plus the flanking sequences encoding the protease 2A recognition cleavage sites were cloned in-frame at the junction of the capsid protein 1D and protease 2A.

Figure 5:
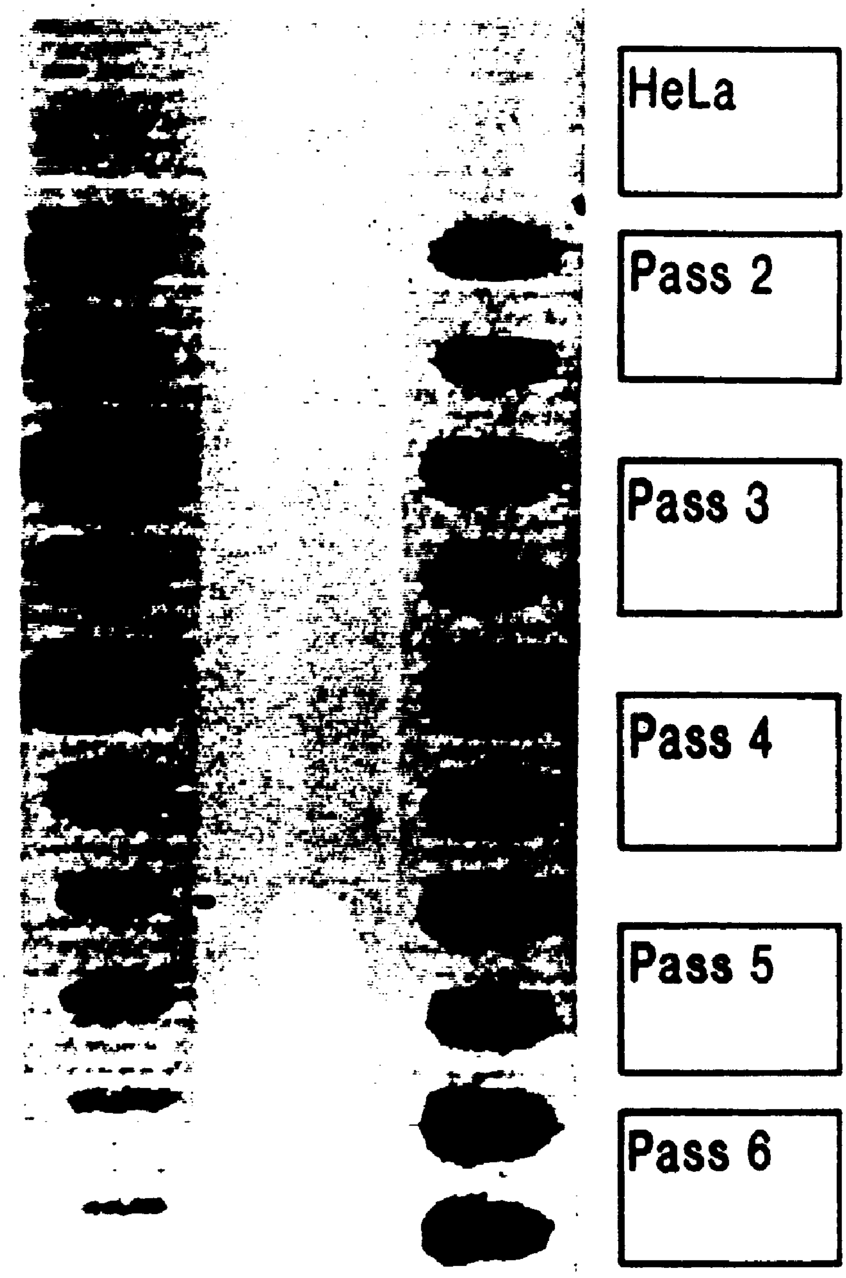
FIG. 5 shows the results of a slot blot of total RNA from HeLa cells inoculated with sequential passages of CVB3/0-IL4 and probed with (left) an mIL4-specific oligonucleotide or (right) a CVB3-specific oligonucleotide. After transfection of the pCVB3/0-IL4 cDNA into HeLa cells and obtaining progeny virus, a stock was made in HeLa cells (pass 1). The stock was used to inoculate a 100 mm dish of HeLa cells at an MOI of 20 (pass 2). After titering, pass 2 was used to inoculate new HeLa cells (pass 3), and so on. To obtain RNA for these experiments, passes 1–5 were used to inoculate a nearly confluent 100 mm dish of HeLa cells at an MOI of 20. Cells were washed after 1 hour, and harvested 5 hours post-infection. Total nucleic acids were digested with DNase. The equivalent of $2\times10^5$ and $0.4\times10^5$ cells were blotted for each passage. The same mass of oligonucleotide probe with equivalent specific radioactivities were used for each strip. Control blots using an alpha-tubulin probe demonstrated each RNA concentration used to be equivalent; RNase treatment of control blots demonstrated no RNA or DNA was detectable.

The construct gave rise to progeny virus (termed CVB3/0-IL4) when electroporated into HeLa cells. Sequence analysis by reverse-transcriptase mediated PCR followed by sequence analysis of the amplimer confirmed that the progeny virus contained the insert and that the viral open reading frame was maintained. The mIL-4 coding sequence in the viral RNA was detected readily by slot blot analysis through 5 passages in HeLa cells, after which deletion occurs rapidly (FIG. 5). This is most likely due to recombination in the 72 nucleotide direct repeat that was engineered to duplicate the protease 2A cleavage sites (see FIG. 1). This is not unexpected: once a CVB3/0 genome deletes the mIl-4 coding sequence, it would be expected to replicate more rapidly, and would rapidly become the dominant quasi species. This may be reflected in the blot following the CVB3 RNA as well: later passages suggest slightly more viral RNA present in the samples.

That the strain CVB3/0-IL4 expressed murine IL-4 in HeLa cells was confirmed by ELISA. Virus was inoculated onto HeLa cells, excess virus was removed by washing at one hour post infection, and the cells were re-fed. At times post-inoculation, the supernatant was removed and then the cells were frozen in a similar volume of fresh medium. Following freezing and thawing and removal of cell debris by centrifugation, the cell medium samples, and the cell fractions were assayed using a commercially available ELISA test for murine IL-4 (BioSource International, Inc.). CVB3/0-IL4 produced mIL-4 intracellularly well above the uninfected control background, reaching 300 pg/ml by 6 hours in cultures producing 106 $TCID_5$ units of virus/ml.

Biological activity of the CVB3/0-IL4 expressed murine IL-4 was assessed using supernatants from HeLa cells infected with the virus, washed with media, incubated for 6–8 hours, then frozen and thawed. Supernatants cleared of cellular debris were assayed for ability to induce MC/9 mouse mast cells to proliferate using an MTT assay (Mosmann T., *J Immunol Methods* 65(1–2):55–63 (1983); and Gieni S, et al., *J Immunol Methods* 187(1):85–93 (1995)) with recombinant mIL-4 as standard. CVB3/0-IL4 HeLa cultures produced 3 units/ml (equivalent to 250 pg/ml of recombinant mIL-4). This compares favorably with reported IL-4 levels in coronary sinus blood concentrations in cardiac transplant patient (229 pg/ml; Fyfe A, et al., *J Am Coll Cardiol* 21(1):171–6 (1993)).

To date, these are the sole data that demonstrate that an interleukin has been cloned successfully in and expressed within the open reading frame of an enterovirus.

EXAMPLE 3

Diminution of CVB4-induced Pancreatic Disease in Mice by Treatment with mIL-4 Expressing CVB3

In an initial test of the ability of the CVB3-IL4 strain to decrease inflammatory disease induced by enteroviruses, a virulent CVB4 strain was used as the inflammatory disease inducer. A different CVB serotype was chosen to minimize the possibility that neutralizing antibodies might reduce the replication of CVB3-IL4 in the doubly-infected mouse (Beck M., et al., *Am. J. Pathol.* 136:669–681 (1990)). The strain of CVB4, termed CVB4-V, was derived by repeated passaging in mice of the avirulent strain, CVB4/P until the virus was repeatedly able to induce severe destruction of the murine pancreatic acinar cells (Ramsingh A., et al, Virus Res 23(3):281–92 (1992)). The pancreatic disease induced by this virus is likely to have an immune component based on the lack of correlation between virulence and the extent of virus replication in the pancreas and the dependence upon host genetic background. Further, it has been demonstrated that CVB4/V is also pancreovirulent in C3H/HeJ male mice, the mice routinely employed to study CVB3 inflammatory heart disease (see Kiel R. J., et al., *European Journal of Epidemiology* 5:348–350 (1989)). In order to determine whether CVB3/0-IL4 would have an effect upon pancreatic disease induced by this strain of CVB4, the experiment outlined in Table 1 was performed.

TABLE 1

OUTLINE OP CVB4/CVB3 EXPERIMENT AND RESULTS IN DISEASE/TOTAL PANCREASES OBSERVED AT DAY 10 PI

| DAY 0 INOC. | DAY 1 INOC. | DAY 3 INOC. | NUMBER OF MICE | DAY 10 PANCREATIC DISEASE |
|---|---|---|---|---|
| MEDIUM | NONE | NONE | 3 | NONE (3) |
| CVB3/0 | NONE | NONE | 4 | SLIGHT (1) SEVERE (3) |
| CVB3/0-1L4 | NONE | NONE | 8 | NONE (7) SLIGHT (1) |
| CVB4/V | NONE | NONE | 5 | SEVERE (5) |
| CVB4/V | CVB 3/0 | NONE | 5 | MODERATE (1) SEVERE (4) |
| CVB4/V | NONE | CVB3/0 | 4 | SEVERE (4) |
| CVB4/V | CVB3/0-1L4 | NONE | 9 | SLIGHT (2) MODERATE 5 SEVERE (2) |
| CVB4/V | NONE | CVB3/0-1L4 | 10 | SLIGHT (2) MODERATE (4) SEVERE (4) |

Figure 6A:
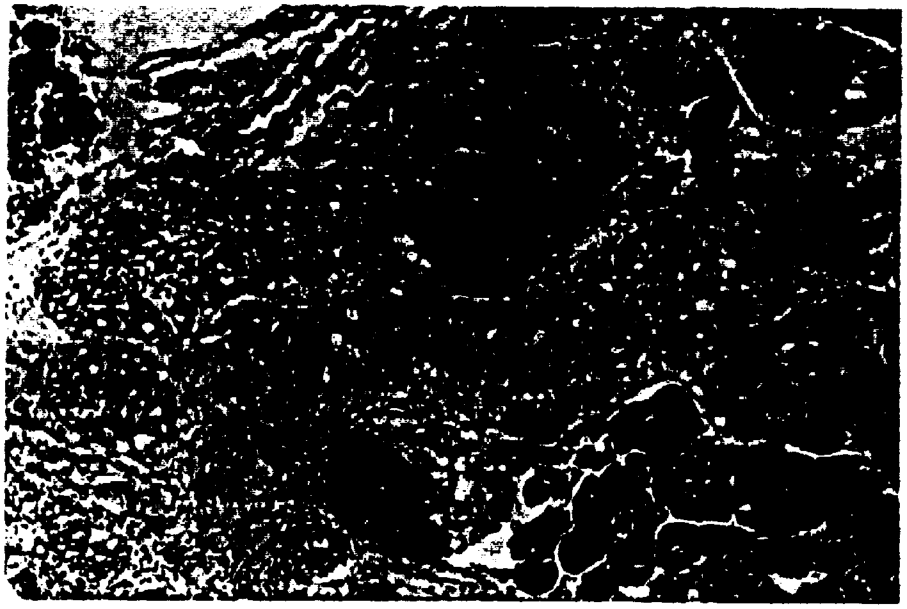
FIG. 6 shows histologic thin sections of murine pancreatic tissue following infection of mice either by CVB3/0 (left-hand panel) or CVB3/0-IL4 (right-hand panel). Mice were sacrificed on day 10 post-infection. CVB3/0 induces severe pancreatic acinar cell destruction; intact acinar cells can be seen in lower right hand corner of the panel. CVB3/0-IL4 does not induce any observable pathologic changes in the murine pancreas (right hand panel).
Figure 6B:

Briefly, mice were inoculated with $5 \times 10^5$ TCID50 units of CVB4/V in 0.1 ml unsupplemented medium. One or three days later, mice were also inoculated with an equivalent dose of CVB3/1IL4 (second passage virus stock after transfection). Control mice were inoculated with the parental (without IL-4 insert and 2A-cleavage site insert) CVB3/0 at the same times. In addition, mice were inoculated with unsupplemented medium without virus or with a single virus: CVB3/IL4, CVB4/V, or CVB3/0. On day 10 post-infection, pancreata were fixed in formalin, sectioned, stained with hematoxylin and eosin, and examined microscopically. Examples of the type of pathologies observed are shown in FIG. 6.

All the mice inoculated only with CVB4/V incurred massive pancreatic damage (Table 1). Mice inoculated with CVB4/V, and that subsequently received CVB3/0-IL4 either on day 1 or day 3 post-infection, demonstrated a significant ablation in the extent of disease. No significant difference was observed between pancreas tissue from mice with day 1 or day 3 post-infection (post CVB4/V) inoculation with CVB3/0-IL4. Mice that were inoculated with CVB4/V and subsequently inoculated with the attenuated parental CVB3/0 strain at either day 1 or 3, demonstrated pancreata that were indistinguishable from the CVB4/V only mice. Thus, the diminution of pancreatic damage observed in mice that received first pancreovirulent CVB4/V, then CVB3/0-IL4 on day 1 or 3 post infection, is due to the expression of the mIL-4 in the chimeric CVB3 strain.

In addition, the CVB3/0-IL4 construct was not virulent for the pancreas. Even though CVB3/0 is completely attenuated for heart disease, it causes significant and widespread destruction of the murine acinar cells. While mice that received only CVB3/0 demonstrated significant pancreatic damage, it is worth noting that the presence of the mIL-4 coding sequence in the CVB3/0 genome resulted in a virus which did not induce pancreatic disease in mice. These data, combined with the data above that showed a diminution of CVB4-caused pancreatic disease by administration of the CVB3/0-IL4 chimera, are consistent with a beneficial role upon pancreatic disease diminution caused by an enterovirus.

EXAMPLE 4

Attenuation of Coxsackievirus B3 Replication by Two Point Mutations in the 5' Non-translated Region In Example 1 we described a conserved 5-nucleotide region, surrounding nt234 of the CVB3 genome, that appears important for replication of the enterovirus genome. In this Example, the molecular grounds for the complete conservation of that 5'-CGUUA (nt 232–236) in the enteroviral 5' non-translated region are examined. Using the well-characterized enterovirus model system, CVB3, point mutations were created at nt233 (G→C) and nt236 (A→U) in the CVB3 5' non-translated region using site specific mutagenesis, according to standard methodology. This double mutant (pCVB3–88) was electroporated into HeLa cells and the progeny virus (CVB3/88) was passaged six consecutive times in HeLa cells. Virus from each passage was assayed in single-step growth curves and by nucleotide sequence analysis.

Prior to passage 3, CVB3/88 was highly attenuated, generating barely detectable titers. Passage 3 CVB3/88 entered log phase replication 3 hours later and achieved final titer 100 fold lower than the parental (control) CVB3 strain. Passage 4 showed an improved rate of replication and final titer 10 fold lower than the parental virus. CVB3/88 passage 5 replication was essentially indistinguishable from the parental strain.

Direct sequence analysis of CVB3/88 RNA using RT-PCR demonstrated that complete reversion had occurred by passage 5, whereas passage 4 virus indicated a partial reversion at nt233(G/C) and complete reversion at nt236 (U→A). Passage 3 showed partial reversion at both sites.

Reacquisition of wild-type replication rate and efficiency is directly correlated with reversion of the mutations to wild-type sequence. The degree of initial attenuation, and concomitant rapidity of reversion argues against robust compensatory mutations arising elsewhere in the viral genome, and is consistent with the previous evidence that this 5 nucleotide tract is absolutely conserved for efficient enteroviral replication.

It should be noted that live, attenuated viruses are useful as vaccines or gene delivery vehicles even if they revert to wild-type through several passages in cultured cells. In fact, live attenuated polioviruses exhibit reversion to wild-type, and these have been used as highly successful oral vaccines for many years. The risk of reversion after a single administration to a living individual (as opposed to several passages in cultured cells) is low, due to the fact that a normal individual will mount an immune response to the virus and clear it from the system before it has the opportunity to replicate to pathogenic levels in a critical target tissue (e.g., neurons). As a result, live, attenuated poliovirus is an effective vaccine even though it reverts to wild-type after passaging through culture cells. Likewise, forms of live, attenuated coxsackievirus and other enteroviruses that may revert to wild-type in culture still will be effective and useful for a variety of purposes. Less reversion-prone viruses, such as the CPV/49 described in Example 1, could be used for purposes where a reversion-prone attenuated virus is inappropriate.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A viral vector comprising a coxsackievirus genome modified to encode an attenuated coxsackievirus, said genome further comprising at least one cloning site for insertion of at least one expressible heterologous nucleic acid.

2. The vector of claim 1, wherein the coxsackievirus genome is a coxsackievirus B genome.

3. The vector of claim 1, wherein the cloning site is positioned between a coding sequence for a capsid protein and a coding sequence for viral protease.

4. The vector of claim 1, wherein the cloning site is positioned at the start of the genome's open reading frame, and wherein the vector further comprises an inserted expressible heterologous nucleic acid comprising a translation start codon and a 3' sequence recognized by a viral protease.

5. The vector of claim 2, wherein the coxsackievirus genome is a coxsackievirus B3 genome.

6. The vector of claim 5, wherein the coxsackievirus genome is modified by altering a transcription regulatory region of the genome.

7. The vector of claim 6, wherein the transcription regulatory region comprises a 5' untranslated region of the genome.

8. The vector of claim 7, wherein the 5' untranslated region is replaced with a 5' untranslated region of a non-enterovirus genome selected from the group consisting of poliovirus and echovirus.

9. The vector of claim 7, wherein a uracil nucleotide at position 234 of the genome is replaced by a cytosine nucleotide or a guanine nucleotide.

10. The vector of claim 7, wherein a guanine nucleotide at position 233 of the genome is replaced by a cytosine nucleotide and an adenine nucleotide at position 236 of the genome is replaced by a uracil nucleotide.

11. The vector of claim 4, wherein the expressible heterologous nucleic acid encodes an antigenic product.

12. The vector of claim 4, wherein the expressible heterologous nucleic acid encodes a biologically active product.

13. The vector of claim 12, wherein the biologically active product is a protein.

14. The vector of claim 13, wherein the protein is a cytokine.

15. A bioengineered virus comprising a Coxsackievirus B3, wherein said coxsackievirus B3 is attenuated, and wherein a genome of said CVB3 contains a coding region for at least one heterologous gene.

16. The bioengineered virus of claim 15, wherein said Coxsackievirus B3 is attenuated through a transcriptional control sequence of the virus genome.

17. The bioengineered virus of claim 15, wherein a cytosine nucleotide is substituted for a uracil nucleotide at position nt234 in said genome of said Coxsackievirus B3.

18. The bioengineered virus of claim 15, wherein a guanosine nucleotide is substituted for a uracil nucleotide at position nt234 in said genome of said Coxsackievirus B3.

19. The bioengineered virus of claim 15, wherein a 5' non-translated region of said genome of said Coxsackievirus B3 is substituted with a 5' non-translated region of a genome from a non-enterovirus.

20. The bioengineered virus of claim 15, wherein said genome of said Coxsackievirus B3 includes one or more sequences selected from the group consisting of SEQ ID No:1, SEQ ID No:2, SEQ ID No:5, SEQ ID No:6, SEQ ID No:7 and SEQ ID No:8.

21. The bioengineered virus of claim 15, wherein a capsid coding region of said genome of said Coxsackievirus B3 has been replaced with at least one heterologous gene.

22. The bioengineered virus of claim 15, wherein said at least one heterologous gene is an immunomodulatory gene.

23. The bioengineered virus of claim 15, comprising up to seven cytokine genes.

24. The bioengineered virus of claim 15, wherein said at least one heterologous gene encodes an antigenic epitope.

25. The bioengineered virus of claim 15, comprising a heterologous immunomodulatory gene and a heterologous gene encoding an antigenic epitope.

26. The bioengineered virus of claim 16, wherein said genome of said Coxsackievirus B3 comprises a basic CVB3/0 genome, wherein said coding sequence for said heterologous gene is inserted between a capsid protein coding sequence and a viral protease coding region site.

27. The bioengineered virus of claim 16, wherein said genome of said Coxsackievirus B3 comprises a basic CVB3/0 genome, wherein said coding sequence for said heterologous gene is inserted directly upstream of capsid protein 1A, starts with the initiation codon AUG, and ends with a sequence recognized by a viral protease.

28. The bioengineered virus of claim 19, wherein said non-enterovirus is selected from the group consisting of poliovirus and echovirus.

29. The bioengineered virus of claim 22, wherein said immunomodulatory gene is a cytokine.

30. The bioengineered virus of claim 29, wherein said cytokine is selected from the group consisting of IL-4 and IL-10.

* * * * *

UNITED STATES PATENT AND TRADEMARK OFFICE

CERTIFICATE OF CORRECTION

PATENT NO. : 6,323,024 B1
DATED : November 27, 2001
INVENTOR(S) : Tracey, S.M. et al.

It is certified that error appears in the above-identified patent and that said Letters Patent is hereby corrected as shown below:

Column 4,
Line 14, please delete "non-enterovirus" and insert therefor -- non-coxsackie enterovirus --.
Lines 15-16, please delete "non-enterovirus" and insert therefor -- non-coxsackie enterovirus --.

Column 21,
Lines 41-42, please delete "non-enterovirus" and insert therefor -- non-coxsackie enterovirus --.

Column 22,
Lines 24 and 56, please delete "non-enterovirus" and insert therefor -- non-coxsackie enterovirus --.

Signed and Sealed this

Twenty-second Day of February, 2005

JON W. DUDAS
*Director of the United States Patent and Trademark Office*

SEQUENCE LISTING

```
<160> NUMBER OF SEQ ID NOS:  18

<210> SEQ ID NO 1
<211> LENGTH: 85
<212> TYPE: DNA
<213> ORGANISM: Coxsackievirus

<400> SEQUENCE: 1

atcactacaa tgacaaatac gggcgcattt ggacaacaat caaggggcag cgtatgtggg     60

gaactacagg gtaatgggtc tcaac                                           85


<210> SEQ ID NO 2
<211> LENGTH: 80
<212> TYPE: DNA
<213> ORGANISM: Coxsackievirus

<400> SEQUENCE: 2

tactcgatca ctacaatgac aaatacgggc gcatttggac aacaatcagg ggcagcgtat     60

gtggggaact acagggtagt                                                 80


<210> SEQ ID NO 3
<211> LENGTH: 34
<212> TYPE: PRT
<213> ORGANISM: Coxsackievirus

<400> SEQUENCE: 3

Ser Gly Val Thr Thr Thr Arg Gln Ser Ile Thr Thr Met Thr Asn Thr
 1               5                  10                  15

Gly Ala Phe Gly Gln Gln Ser Gly Ala Val Thr Leu Glu Met Pro Gly
            20                  25                  30

Ser Ala


<210> SEQ ID NO 4
<211> LENGTH: 25
<212> TYPE: PRT
<213> ORGANISM: Coxsackievirus

<400> SEQUENCE: 4

Met Lys Ser Asn Ser Ile Thr Thr Met Thr Asn Thr Gly Ala Phe Gly
 1               5                  10                  15

Gln Gln Ser Gly Ala Val Tyr Val Gly
            20                  25


<210> SEQ ID NO 5
<211> LENGTH: 27
<212> TYPE: DNA
<213> ORGANISM: Coxsackievirus

<400> SEQUENCE: 5

atgggaaatt cgagctcgat gcctggc                                         27


<210> SEQ ID NO 6
<211> LENGTH: 28
<212> TYPE: DNA
<213> ORGANISM: Coxsackievirus
```

-continued

<400> SEQUENCE: 6
atgaaaagcg catgcgggtt ttcaaggt 28

<210> SEQ ID NO 7
<211> LENGTH: 74
<212> TYPE: DNA
<213> ORGANISM: Coxsackievirus

<400> SEQUENCE: 7
actactaggc aaagcatcac tacaatgaca aatacgggcg catttggaca acaatcaggg 60
cagtctcgga tcca 74

<210> SEQ ID NO 8
<211> LENGTH: 62
<212> TYPE: DNA
<213> ORGANISM: Coxsackievirus

<400> SEQUENCE: 8
gaattctgca gatcaattac caccatgacc aacacggggc gcatttggac aatcaggggc 60
ag 62

<210> SEQ ID NO 9
<211> LENGTH: 5
<212> TYPE: PRT
<213> ORGANISM: Coxsackievirus

<400> SEQUENCE: 9

Asn Thr Gly Ala Phe
1 5

<210> SEQ ID NO 10
<211> LENGTH: 11
<212> TYPE: PRT
<213> ORGANISM: Coxsackievirus

<400> SEQUENCE: 10

Tyr Arg Val Met Gly Leu Asn Tyr Ser Ile Thr
1 5 10

<210> SEQ ID NO 11
<211> LENGTH: 58
<212> TYPE: PRT
<213> ORGANISM: Coxsackievirus

<400> SEQUENCE: 11

Ser Gly Val Thr Thr Thr Arg Gln Ser Ile Thr Thr Met Thr Asn Thr
1 5 10 15

Gly Ala Phe Gly Gln Gln Ser Gly Ala Val Thr Leu Glu Asp Pro Arg
20 25 30

Val Pro Ser Ser Asn Ser Ile Thr Thr Met Thr Asn Thr Gly Ala Phe
35 40 45

Gly Gln Gln Ser Gly Ala Val Tyr Val Gly
50 55

<210> SEQ ID NO 12
<211> LENGTH: 59
<212> TYPE: PRT
<213> ORGANISM: Coxsackievirus

<400> SEQUENCE: 12

Ser Gly Val Thr Thr Thr Arg Gln Ser Ile Thr Thr Met Thr Asn Thr

-continued

```
 1               5                  10                  15

Gly Ala Phe Gly Gln Gln Ser Gly Ala Val Thr Leu Glu Met Pro Gly
            20                  25                  30

Ser Ala Met Lys Ser Asn Ser Ile Thr Thr Met Thr Asn Thr Gly Ala
        35                  40                  45

Phe Gly Gln Gln Ser Gly Ala Val Tyr Val Gly
    50                  55


<210> SEQ ID NO 13
<211> LENGTH: 69
<212> TYPE: DNA
<213> ORGANISM: Coxsackievirus

<400> SEQUENCE: 13

atgggaaatt cgagctccgt acccggggat cctctagagt cgacctgcag gcatgcgggt     60

tttcaagga                                                              69


<210> SEQ ID NO 14
<211> LENGTH: 55
<212> TYPE: DNA
<213> ORGANISM: Coxsackievirus

<400> SEQUENCE: 14

atgggaaatt cgagctcgat gcctggcatg aaaagcgcat gcgggttttc aaggt          55


<210> SEQ ID NO 15
<211> LENGTH: 23
<212> TYPE: PRT
<213> ORGANISM: Coxsackievirus

<400> SEQUENCE: 15

Met Gly Asn Ser Ser Ser Val Pro Gly Asp Pro Leu Glu Ser Thr Cys
 1               5                  10                  15

Arg His Ala Gly Phe Gln Gly
            20


<210> SEQ ID NO 16
<211> LENGTH: 18
<212> TYPE: PRT
<213> ORGANISM: Coxsackievirus

<400> SEQUENCE: 16

Met Gly Asn Ser Ser Ser Met Pro Gly Met Lys Ser His Ala Gly Phe
 1               5                  10                  15

Gln Gly


<210> SEQ ID NO 17
<211> LENGTH: 138
<212> TYPE: DNA
<213> ORGANISM: Coxsackievirus

<400> SEQUENCE: 17

actactaggc aaagcatcac tacaatgaca aatacgggcg catttggaca acaatcaggg     60

gcagtctcgg atccagaatt ctgcagatca attaccacca tgaccaacac gggggcgcat    120

ttggacaatc aggggcag                                                  138


<210> SEQ ID NO 18
<211> LENGTH: 46
<212> TYPE: PRT
<213> ORGANISM: Coxsackievirus
```

-continued

```
<400> SEQUENCE: 18

Thr Thr Arg Gln Ser Ile Thr Thr Met Thr Asn Thr Gly Ala Phe Gly
 1               5                  10                  15

Gln Gln Ser Gly Ala Val Ser Asp Pro Glu Phe Cys Arg Cys Ile Thr
            20                  25                  30

Thr Met Thr Asn Thr Gly Ala Phe Gly Gln Ser Gly Ala Val
        35                  40                  45
```